United States Patent [19]
Talley et al.

[11] Patent Number: 6,132,955
[45] Date of Patent: Oct. 17, 2000

[54] METHOD FOR DERIVITIZING ELECTRODES AND ASSAY METHODS USING SUCH DERIVITIZED ELECTRODES

[75] Inventors: David Talley, Olney; Jonathan K. Leland, Silver Spring; Gary F. Blackburn, Gaithersburg, all of Md.

[73] Assignee: IGEN International, Inc., Gaithersburg, Md.

[21] Appl. No.: 08/922,761

[22] Filed: Sep. 3, 1997

Related U.S. Application Data

[63] Continuation of application No. 08/443,497, May 18, 1995, abandoned.

[51] Int. Cl.$^7$ .................................................. C12Q 1/00
[52] U.S. Cl. ............. 435/4; 435/5; 435/6; 435/7.1; 435/7.7; 435/817; 436/526; 436/518; 204/400; 204/403
[58] Field of Search ...................... 204/400, 403; 435/4–6, 7.1, 7.7, 817; 436/526, 578

[56] References Cited

U.S. PATENT DOCUMENTS

| | | |
|---|---|---|
| 4,554,088 | 11/1985 | Whitehead et al. . |
| 4,628,037 | 12/1986 | Chagnon et al. ................. 436/526 |
| 4,655,885 | 4/1987 | Hill et al. ................... 204/72 |
| 4,695,392 | 9/1987 | Whitehead et al. . |
| 4,695,393 | 9/1987 | Whitehead et al. . |
| 4,698,302 | 10/1987 | Whitehead et al. ................ 435/94 |
| 4,882,057 | 11/1989 | Broderick ................. 128/631 |
| 4,945,045 | 7/1990 | Forrest et al. ............ 435/25 |

FOREIGN PATENT DOCUMENTS

| | | |
|---|---|---|
| 0180384 | 5/1986 | European Pat. Off. . |
| 2105750 | 3/1983 | United Kingdom . |
| 86/02734 | 5/1986 | WIPO . |
| 87/00987 | 2/1987 | WIPO . |
| 88/03947 | 6/1988 | WIPO . |
| 89/04919 | 6/1989 | WIPO . |
| 05301 | 5/1990 | WIPO . |
| 00982 | 2/1992 | WIPO . |
| 92/14138 | 8/1992 | WIPO . |

OTHER PUBLICATIONS

Blackburn et al. "Electrochemiluminescence Detection for Development of Immunoassays and DNA Probe Assays for Clinical Diagnostics," 37, Clinical CHemistry 1534–1539 (1991).

*Primary Examiner*—Sheela Huff
*Attorney, Agent, or Firm*—Whitman Breed Abbott & Morgan LLP

[57] ABSTRACT

An electrode can be derivitized by contacting it with a derivitizing solution to make it more sensitive to a desired analyte signal as opposed to interfering signals in an assay. Particularly, in an electrochemiluminescence (ECL) immunoassay the working electrode can be derivitized to be more sensitive to desired analyte signals, as opposed to interfering non-bound conjugate or serum matrix signals.

22 Claims, 11 Drawing Sheets

METHOD FOR DERIVITIZING ELECTRODES AND ASSAY METHODS USING SUCH DERIVITIZED ELECTRODES

This application is a continuation of application Ser. No. 08/443,497, filed May 18, 1995, now abandoned.

The present invention relates to a method for derivitizing electrodes, the resulting electrodes and to assay methods utilizing such derivitized electrodes. Particularly, it is directed to an electrochemiluminescent (ECL) method for performing immunoassays, particularly homogeneous immunoassays, wherein derivitized electrodes are used.

BACKGROUND OF THE INVENTION

Assays which make use of electrodes for the detection and quantitation of certain materials in a solution, e.g. immunoassays for detection and quantitation of antigens, are known in the art. For instance, electrochemiluminescence is the basis for highly sensitive detection and quantitation processes in which reactive species are electrochemically generated from stable precursors at the surface of an electrode. The electrochemically generated reactive species undergo a chemiluminescent reaction. The luminescence from the chemiluminescent reaction is used to detect or quantify ECL-active species, which have been bound to materials desired to be detected, i.e. the analyte. For example, the ECL-active species may be bound to an antibody for detection of an antigen specific to the antibody. Highly sensitive electrochemiluminescence detection systems and methods have been developed which are capable of measuring trace amounts of materials. The detection of luminescence from ECL-active labels has been used to develop assays in materials such as biochemical and biological substances and provide sensitive immunoassays and DNA probe assays.

Other types of assays making use of an electrode include, for example, amperometric and potentiometric assays.

These electrochemiluminescent detection systems have many advantages over other detection systems in that measurement is simple and rapid, no radioisotopes are used, the detection limits for ECL-active species are extremely low (200 fmol/L); the dynamic range of the ECL-active specific quantification extends over six orders of magnitude; and the ECL-active labels are extremely stable and small (~1000 Da) so that haptens or large molecules can be labeled and multiple labels can be coupled to proteins or oligonucleotides without affecting their immuno-reactivity, solubility or their ability to hybridize.

In addition, since the chemiluminescence requires an applied voltage, the initiation and duration of the response can be controlled by controlling the voltage applied to an electrode.

ECL detection apparatus and methods are described in more detail in the following PCT published applications: WO 86/02734, WO 87/00987, WO 88/03947. See also, Massey, Biomedical Products: Tools & Techniques, October 1992; and, Blackburn et al., Clinical Chemistry, Vol. 37, No. 9; p. 1534–1539 (1991).

PCT Published Application WO 90/05301 describes methods for performing assays based on luminescent phenomena in a homogeneous format wherein modulation of the intensity of the luminescent signal generated by the ECL-active moiety provides a means for monitoring the specific binding of an assay system. In these methods, microparticles are bound to ECL-active species of the assay components to modulate the intensity of the luminescent signal.

PCT Published Application WO 92/00982 describes methods for performing assays wherein the microparticles bound to the ECL-active species are magnetically responsive and are drawn to the electrode where the ECL-active moiety undergoes excitation by a plurality of north-south oriented magnets. This significantly enhances the ECL signal from the sample composition.

A variety of formats have been developed for assays based on the detection and quantitation of electrochemiluminescence. For example, heterogenous (one or more separations) and homogeneous (non-separation) formats have been developed for competitive assays where, for example, haptens labeled with an ECL-active moiety compete for antibody with an analyte of interest. In a heterogenous format, the free and bound fractions of the labeled component such as hapten are separated before analysis in the ECL detection apparatus.

In homogeneous formats, there is no separation of fractions before the analysis. Such a format can be used when the efficiency of ECL excitation differs considerably for the free and bound fractions of the labeled components. For example, a homogeneous immunoassay may involve adding a serum sample into a composition of specific reagents, incubating the mixture and measuring for the analyte with an immunoanalyzer without any separation or washing steps. Homogeneous immunoassays, also referred to as nonseparation immunoassays, provide the advantage of eliminating the separation steps and, thus, simplifying and decreasing the time required for the assay.

However, problems in homogeneous immunoassays can arise due to interference with the desired analyte signal by serum matrix components and unbound conjugates. Interference with the analyte signal could also arise in heterogeneous immunoassays wherein the separation(s) conducted do not remove all or significant amounts of the interfering serum matrix components and unbound conjugate components.

While the apparatus and methods taught in the prior art such as WO 90/05301 and WO 92/0982 and commercial apparatus such as the Origen® 1.5 analyzer by IGEN Inc. permit detection and quantitation of extremely small quantities of analytes in a variety of assays, there is a continuing effort to lower the detection limits and increase the sensitivity of assays performed and also to increase the speed at which assays are performed. Further, it would be advantageous to be able to perform homogeneous immunoassays, or heterogeneous immunoassays requiring fewer separation steps and, thus, less time, upon analytes which heretofore were not amenable to such assays due to the presence of serum matrix components and unbound conjugates which interfere with the desired analyte signal.

BRIEF DESCRIPTION OF THE DRAWINGS

Various objects, features and attendant advantages of the present invention will be more fully appreciated as the same becomes better understood when considered in conjunction with the accompanying drawings, in which like reference characters designate the same or similar parts throughout the several views, and wherein.

SUMMARY OF THE INVENTION

Figure 1:
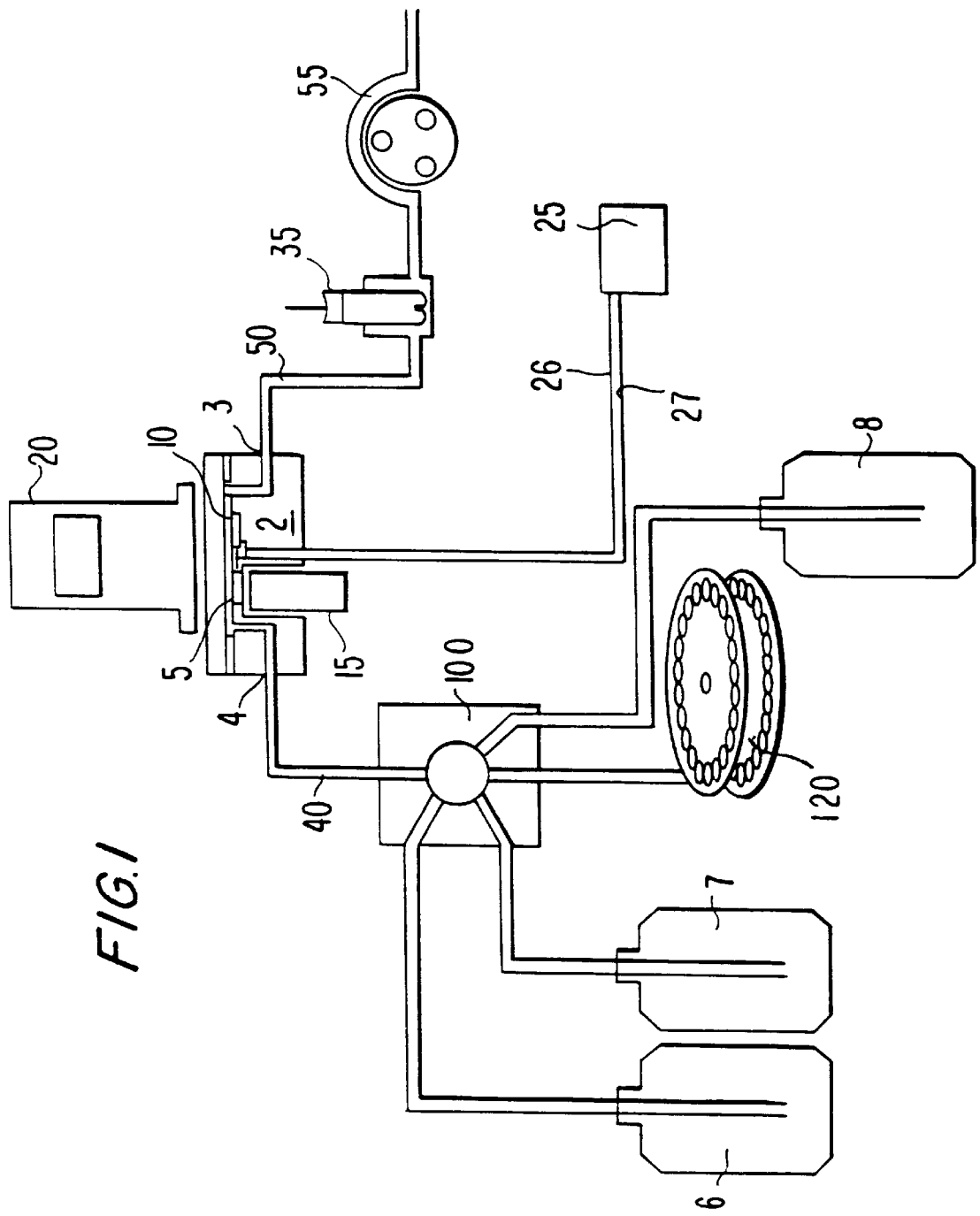
FIG. 1 is a schematic representation of the basic configuration of an ECL detection system of the present invention.

This invention provides a process for derivitizing electrodes. For example, electrodes can be made more sensitive to analyte signals, as opposed to interfering non-bound conjugate or serum matrix signals in assays. The assay methods will thus have improved sensitivity and faster assay times, particularly an electrochemiluminescent immunoassay method having such advantages.

The invention further provides an assay for determining an analyte in a sample using an electrode, which comprises contacting said electrode with a derivitizing agent such that in the subsequent determination of the analyte, using the electrode to generate a signal from the analyte, the signal from at least one non-analyte component in the sample is decreased. Particularly, an assay for determining an analyte in a sample composition using a working electrode, which comprises:

a) contacting the working electrode with a derivitizing agent;

b) contacting the sample composition with the working electrode;

c) collecting the analyte on the working electrode by suitable means; and d) applying a voltage to said electrode such that a signal for determination of the analyte is generated;

wherein the signal from at least one non-analyte component is decreased. Decreasing of the non-analyte signal is meant to encompass decreasing such signal relative to the analyte signal and/or decreasing such signal in absolute terms, as compared to the signal from non-analyte components when the electrode is not contacted with a derivitizing agent. The signal which is generated is any signal which can be used to determine the analyte of interest by any suitable means.

Even more particularly, this assay may be conducted wherein the electrochemical cell is part of an electrochemiluminescence (ECL) immunoanalyzer, said sample composition contains the analyte bound to an ECL-active species comprising an ECL-active moiety, and an ECL-interfering species comprising at least one ECL-active species not bound to the analyte and/or at least one ECL-interfering serum matrix component, a luminescence signal is, generated by applying a voltage to said working electrode of sufficient magnitude to induce luminescence from the ECL-active species within the sample composition; wherein the luminescence signal from at least one ECL-interfering species is decreased. By "ECL-interfering species", it is meant any species not bound to the analyte which produces an ECL signal which lessens in any way the ability or sensitivity of the ECL signal from the analyte. The ECL signal can be used by conventional methods to determine the analyte.

Also the invention provides a method for lowering undesired signals from non-analyte components in an assay of a sample containing an analyte using an electrode which comprises, contacting the electrode with a derivitizing agent such that said undesired signals are lowered.

The invention is further directed to an electrode having one or more layers thereon formed by contacting the electrode with a derivitizing agent, for example, an agent comprising linolenic acid, linoleic acid, oleic acid, eicosatrienoic acid, undecylenic acid, stearic acid, or capric acid or salts thereof or thiols, for example, cystamine dihydrochloride or mixtures thereof.

By "determining" an analyte it is meant any form of detecting, quantifying, identifying, confirming and/or ascertaining the analyte whether or not other steps are also conducted.

Electrodes may be derivitized by contacting them with a derivitizing solution while maintaining a derivitizing effective voltage across the working electrode surface. The derivitizing solution provides chemical moieties which bind to the electrode forming one or more layers thereon and the inventors have discovered that such derivitization reduces interfering signals from unbound conjugates and other serum matrix components when performing assays. Also, the invention accomplishes the objective of providing improved assays, particularly ECL immunoassays, in that the derivitization of the electrodes results in increased sensitivity of the assay to the desired analyte signal as opposed to interfering signals from, for example, unbound conjugates and serum matrix components.

Upon further study of the specification and appended claims, other objects and advantages of this invention will become apparent to those skilled in the art.

Preferred as derivitizing solutions are those which contain fatty acids and salts thereof as the derivitizing agent, such as sodium and potassium salts. The salts may be formed in situ from the acids in an assay buffer solution. Fatty acids containing 10–20 carbon atoms are preferred, for example. Particularly preferred are linolenic acid, linoleic acid, oleic acid, eicosatrienoic acid, undecylenic acid, stearic acid, or capric acid or salts thereof or mixtures thereof. Further preferred are $C_{18}$ unsaturated fatty acids or their salts, preferably of 1–3 double bonds, with effectiveness increasing from one (oleic) to three (linolenic) double bonds. Also, useful are derivitizing solutions which have sulfur-containing compounds, for example, short-chain aminated thiols, particularly amine-terminated thiols, for example, of 1–6 carbon atoms, particularly 2–4 carbon atoms, as the derivitizing agent. Cystamine dihydrochloride is particularly preferred. Other solutions useful as derivitizing solutions are those containing the thiols 3,3'-dithiopropionic acid and 1-thio-B-D-glucose tetracetate. Also, useful are surfactants, such as 4-lauryl ether, dodecyl maltoside and tetramethyl-5-decyn-4,7-diol.

Although not intending to be bound by this theory, it is believed that the derivitizing agents derivitize the electrode by binding to the electrode surface, for example the acids may bind in their ester form, i.e., oleic acid binds as oleate to the electrode, to form layers of the bound derivitizing agent on the surface of the electrode. It is believed that the layers act to decrease interfering signals from non-analyte components, also, the derivitized surface charge properties have an effect in decreasing interfering signals.

There is a potential problem with formulation stability of the derivitizing agent in solution, i.e. linoleic acid in assay buffer. The formulation instability is seen mostly in the solution appearance, i.e. color, an not in its effectiveness for electrode derivitization. The discoloration may be noticeable after about 2–4 weeks, while small changes in effectiveness, if any, may occur after 2–3 months. The instability is caused primarily by increased temperature above 4° C. and less so by exposure to light.

The derivitized electrodes are particularly useful in assay processes, particularly immunoassays, but also for DNA probe assays, which utilize an electrochemical cell with electrodes. When used in such assays the method of integration and assay may include the following steps:

a) contacting a working electrode of the electrochemical cell with a derivitizing solution containing a derivitizing agent, particularly while applying a derivitizing effective voltage across the electrode such that the agent binds to the working electrode, b) introducing a sample composition containing an analyte to be determined into the electrochemical cell containing the working electrode;

c) collecting the analyte on a surface of said electrode by suitable means; and d) imposing a voltage on said electrode in a manner which provides a signal for detection and quantitation of the analyte;

wherein the derivitizing agent bound to the surface of the electrode decreases any signal measured from non-analyte components.

Examples of means for collecting the analyte on the surface of the electrode include using a magnetic field to attach the analyte. Examples of the manner in which a signal can be generated by imposition of a voltage on the electrode include ECL measurement where the analyte contains an ECL-active species.

The invention applied to the embodiment of electrochemiluminescence assays provides a method for measuring electrochemiluminescence from a sample composition in an electrochemiluminescent (ECL) immunoanalyzer, wherein said sample composition contains an analyte bound to an ECL-active species, comprising an ECL-active moiety and, optionally, a magnetically responsive particle, and an ECL-interfering species, comprising at least one unbound ECL-active species and/or at least one ECL-interfering serum matrix component, said method comprising:

a) contacting a working electrode of the ECL-immunoanalyzer with a derivitizing solution containing a derivitizing agent, particularly while applying a derivitizing effective voltage across the electrode such that the agent binds to the surface of the working electrode, b) introducing said sample composition into a measurement cell of the ECL-immunoanalyzer which contains the working electrode;

c) collecting the analyte bound to an ECL-active species that comprises an ECL-active moiety on the working electrode, for example, by imposition of a magnetic field when the ECL-active species is attached to magnetically responsive particles;

d) imposing a voltage on said electrode of sufficient magnitude to induce luminescence from the bound ECL-active species within the sample composition; and e) measuring the luminescence emitted from the sample composition, wherein the derivitizing agent bound to the surface of the electrode decreases the luminescence signal measured from at least one unbound ECL-active species and/or from at least one interfering matrix component, in relation to the desired analyte signal.

Several different heterogeneous and homogeneous formats to collect and concentrate the complex on the surface of an electrode can be employed in performing the method described above. In a homogeneous assay, the bound fraction is concentrated on the surface of the working electrode and the ECL signal is measured in the presence of the unbound fraction in the measurement cell. In a modified heterogeneous format, an in situ separation step is performed after the sample composition has been pumped into the measurement cell and the bound fraction is captured on the working electrode. In this in situ separation step, a second fluid is pumped through the cell to separate the unbound fraction from the bound fraction of the ECL-active species. The ability to perform the separation of the bound and unbound fractions inside the measurement cell is advantageous in that it does not require additional separation apparatus and the procedure is generally much faster than external separation methods. Measuring the ECL signal from the bound fraction after such a separation step provides greater accuracy and lower detection limits than is possible without separation. The present invention is more particularly suited in connection with a homogeneous immunoassay because, in the absence of a separation step, the sample will contain unbound conjugate and serum matrix components which may generate an interfering signal, thus, making the assay less sensitive to the desired analyte signal. The derivitization of the electrode according to the invention decreases this interfering signal.

FIG. 1 illustrates the primary components of a conventional ECL detection system usable in modified form for this invention. The heart of the instrument is the cell 2, an electrochemical flow cell as shown, containing a working electrode 5, a counter electrode 10 and a magnet 15.

Figure 2:
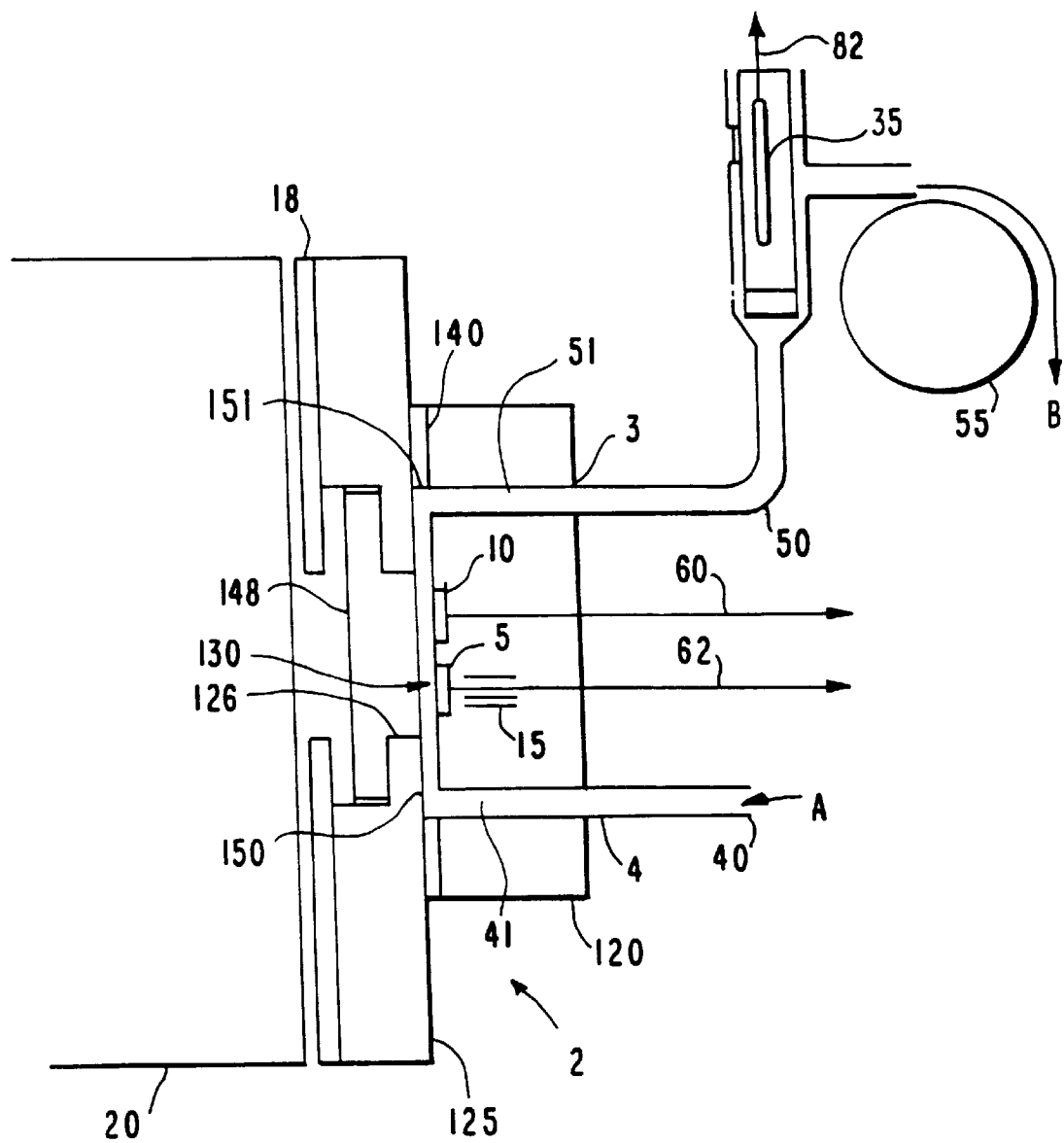
FIG. 2 is a schematic representation of a flow cell of an ECL detection apparatus of the present invention and the components of the ECL detection apparatus which interact with the flow cell.

FIG. 2 provides a more detailed illustration of an electrochemical flow cell that can be used in modified form for the present invention. Working electrode 5 and counter electrode 10 initiate the ECL reaction when a voltage is applied thereto by a voltage source. Preferably, these electrodes are fabricated from gold but other materials have been used with various degrees of success. A light detection means 20 detects the light emitted during the ECL reaction and may advantageously be a photomultiplier tube (PMT), photodiode, charge coupled device photographic film or emulsion or the like. A reference electrode 35 is placed in a fluid path 50 downstream from flow cell 2. A pump 55 draws various fluids through flow cell 2 via fluid path 50. Fluid path 50 can be a simple conduit which leads from an outlet 3 of flow cell 2. Sample compositions are introduced to the flow cell by a fluid path 40 through an inlet 4. Fluid path 40 can be a simple conduit which feeds fluids from a fluid control means. The fluid control means controls the fluid which enters flow cell 2 from various sources. In FIG. 1, bulk sources 6 and 7 are shown, which can be bulk sources of cleaning solution and/or conditioning solution for flow cell 2 and bulk source 8 for the derivitizing agent solution, and also a sample source 120 for sample compositions, which can be a test tube array. Voltage source 25 is typically a potentiostat that can apply various voltage wave forms through the electrodes via leads 26 and 27.

Figure 3:
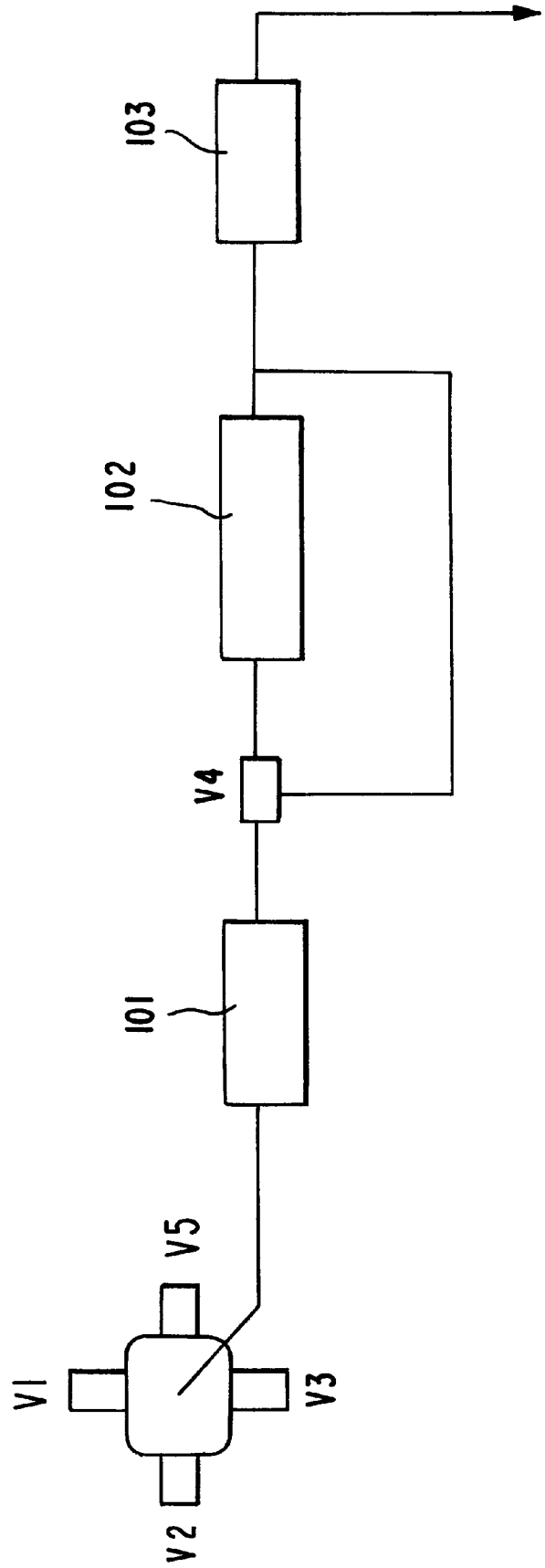
FIG. 3 is a schematic representation of a configuration for performing derivitization of electrodes according to the present invention.

FIG. 3 shows an embodiment of a modification to the above apparatus for facilitating the inventive method. Therein, the fluid control means is provided with an additional valve V5 for provision of the derivitizing solution, as well as a valve, V1, for the assay buffer, a valve, V2, for the cell cleaner solution and, a valve, V3, used to introduce air during the cleaning cycle, if desired. Also, the figure depicts optional embodiments wherein a heater, 101, is provided between the fluid control means and the cell and wherein a bypass valve V4 is provided for bypassing of the cell, 102, for the purpose of air bubble removal, for example. A pump, 103, provides the means for drawing the various solutions through the cell. The cell cleaner solution can be any cell cleaner solution conventionally known for cleaning electrodes and an electrochemical cell flow path.

This invention can employ fluid handling components, luminometers and potentiostats found in the commercially available ECL detection systems, such as the components employed in the Origen® 1.5 analyzer by IGEN, Inc., Rockville, Md.

In a typical sequence for an ECL immunoassay, the cell is preconditioned by flowing an assay buffer solution or other suitable solution therethrough, such as drawn through valve V1. Then the electrode is derivitized by flowing the derivitizing solution from bulk source of, preferably mixed with buffer solution, through the cell. The sample composition is then drawn from the sample source 120, typically within a test tube, and into flow cell 2 via a vacuum provided by pump 55. The magnetically responsive particles within the sample composition are captured on electrode 5 by a magnetic field from magnet 15. Optionally, for a heterogeneous or modified heterogeneous format, before application of the voltage to generate an ECL signal, the particles are washed, e.g. with assay buffer, to remove part of the ECL active compounds which are not bound to the magnetically responsive particles. These include free or unbound ECL active compounds and ECL active components which are engaged in non-specific binding, i.e., the particles are not bound to the ECL active moiety at the specific site of interest.

For ECL measurement, the magnetic field is removed from the cell and a ramp voltage is applied to working electrode 5 and counter electrode 10 via potentiostat 25 and emitted light is measured with photomultiplier tube 20. Following measurement, cleaning solution through V2 and/or an assay/buffer solution, as a conditioning solution, through V1 may be drawn into cell 2 from source 6 and/or 7 via controller 100, if desired. A voltage wave form is typically applied when the assay/buffer solution is within the cell to "condition" or standardize the surface of the electrode to provide reproducible measurements. In preferred embodiments, the manipulation of the fluid handling components for the samples, cleaning solution and/or conditioning solution is automated.

FIG. 2 shows a more detailed illustration of the cell 2 and reference electrode 35. The apparatus shown in FIGS. 1–3 incorporate a flow-through cell. However, one skilled in the art will recognize that a static cell can be easily incorporated in these detection systems and that the present invention encompasses such apparatus, although they are not preferred. The light detection means 20 can be any of the embodiments described above for the apparatus in FIG. 1, but is preferably a photomultiplier tube (PMT). The apparatus includes a pump 55, which is also advantageously a peristaltic pump, which provides means for fluid transport to, through and from the cell 2. A positive displacement pump can also be used. A shutter mechanism 18 is provided between cell 2 and PMT 20 and is optional. Preferably, the shutter 18 is controllably operated to open only so far as to expose PMT 20 to cell 2 during ECL measurement. The shutter mechanism may be closed, for example, during maintenance. Cell 2 comprises mounting blocks 120 and 125, an annular spacer 140, and a window 148. A sample holding volume 130 is defined by mounting block 120 and 125, annular spacer 140 and window 148. Mounting blocks 120 and 125 are advantageously constructed of stainless steel, annular ring 140 is advantageously constructed of Teflon® and window 148 is advantageously formed with a material which is substantially transparent at the wavelength of electrochemical luminescent light emitted by the ECL active species in the cell such as glass, plastic, quartz or similar material. Mounting block 125 has a central aperture 126 in which window 148 is seal fitted. Mounting block 120 is connected to an inlet tube 40 at an inlet 4 and outlet tube 50 to an outlet 3 which are both preferably constructed of stainless steel. Inlet tube 40 feeds an inlet channel 41 and outlet tube 50 receives from outlet channel 51 within mounting block 120. Inlet channel 41 and outlet channel 51 open into sample holding volume 130. Inlet channel 41 intersects sample holding volume 130 at a first end 150 thereof adjacent to the spacer 140 and outlet channel 51 intersects sample holding volume 130 at a second end 151 thereof, adjacent spacer 140. The combination of inlet tube 40, inlet channel 41, sample holding volume 130, outlet channel 51, and outlet tube 50, thereby provides a continuous flow path for the narrow, substantially laminar flow of the sample composition to, through and from cell 2. Arrows A and B represent the flow into and out of inlet tube 40 and outlet tube 50, respectively.

Pump 55 is advantageously positioned at outlet tube 50 to pull solution from a sample volume in the direction of arrow A into inlet tube 40. The solution will flow through inlet tube 40, sample holding volume 130 and outlet tube 50 past reference electrode 35 and out in the direction of arrow B. Alternatively, pump 55 may be positioned at inlet tube 40 to push the solution through inlet tube 40, sample volume 130 and outlet tube 50. Pump 55 may be controlled to suspend its operation to hold a particular solution in cell 2 for a period of time. Advantageously, the same flow path through the inlet tube, sample holding volume and outlet tube is used for all solutions and fluids which pass through cell 2, thereby a fluid performs a hydrodynamic cleaning action, forcing the previous fluid out of cell 2. The flow through construction permits the rapid alternation between initialling steps, including the derivitization step, and allows the working electrodes to be impressed with a variable voltage or continuously held at a preoperative potential while continuously exposed to one or more solutions without exposing these electrodes to air, which can cause random voltage fluctuations.

Mounted within sample holding volume 130 is a working electrode 5 and counter electrode 10. In other embodiments, multiple working electrodes may be utilized. These electrodes may be advantageously constructed of platinum, gold, carbon or other materials which are effective for this purpose. A gold flanking electrode arrangement may also be used effectively.

Working electrode 5 and counter electrode 10 provide the interface to impress the potential on the solution within the sample holding volume 130 which energizes the chemical reactions and triggers electrochemiluminescence in this sample and/or provides energy for cleaning, conditioning and derivitizing the surfaces of the cell 2 and the electrodes. Working electrode 5 is where the electrochemical and ECL reactions of interest take place.

Reference electrode 35 provides a reference voltage to which the voltage applied by the working electrode 5 is referred, for example, +1.2 volts versus the reference, and is advantageously located in outlet tube 50 at a position remote from cell 2. Wire leads 60, 62 and 82 connect working electrode 5, counter electrode 10 and reference electrode 35, respectively, to a voltage control source, which is not shown. Suitable voltage control sources include the conventional potentiostats and operating circuits described in Published PCT Appln. Wo 82/14138.

The ECL method involves derivitizing the working electrode by passing a derivitizing solution through a sample cell containing the electrode; introducing a sample composition into the sample cell, wherein said sample composition contains magnetically responsive suspended particles with an ECL-active moiety bound thereto; imposing a magnetic field on the sample composition of sufficient strength to collect magnetically responsive particles at the surface of an electrode; imposing a voltage on said electrode sufficient to induce the ECL-active compound to luminesce and measuring the emitted luminescence.

This method can be advantageously performed with the apparatus of the present invention such as that shown in FIG. 1 modified per FIG. 3, wherein a derivitizing solution is drawn through valve V5 through the cell to derivitize the working electrode. A voltage of from 0 to 565 mV is applied to the electrode for derivitization. For example, a voltage of 565 mV is preferred. The derivitizing solution flow is then halted and a sample is drawn from carousel 120 via sample control means 100 and introduced to the cell 2. The magnetically responsive particles are collected on the surface of working electrode 5 with magnet 15. Optionally, additional buffer solution may then be pumped through the cell, e.g. at a flow rate of 2.5 ml/min for 20 seconds. If pivotally anchored, magnet is preferably in the up position and following the collection of magnetically responsive particles, the magnetic 15 is retracted from the up position to release the magnetic particles. Optionally, the pump is turned off once particles are collected on the electrode surface and the sample composition is in the static state while a voltage is applied to electrode 5 and counter electrode 10 sufficient to induce luminescence. A photomultiplier tube then measures the luminescence emitted from the sample composition. After measurement, the sample cell may be purged of sample composition with a cleaning solution. Where pivotally anchored, the magnet can be retracted from the surface of the electrode to release the magnetically responsive particles. Following the cleaning process and release, an assay/buffer solution may be introduced to the sample cell and a voltage applied to condition the electrode surface for the next measurement.

The derivitizing solution is preferably passed through the cell diluted with assay buffer solution. The "assay buffer" solution may be any solution which provides a buffer effect for the assay method and such solutions are conventionally known. The concentration of the derivitizing agents, the flow rate of the derivitizing agent solution and the time of the treatment may be varied to obtain differing degrees of derivitization of the electrode and the invention is not limited to any particular combination of derivitization conditions. As an example, the concentration of the derivitizing agent may be from 0.01 to 0.2%, particularly preferably 0.03%, depending on the type of agent and degree of derivitization desired. Preferably, the derivitizing/assay buffer solution is passed through the cell at a flow rate of from 1 to 3, particularly preferably 2.5, ml/min, for from 5 to 20 seconds, particularly preferably 10 seconds. Using linolenic acid as the derivitizing agent, the electrode derivitization can be conducted in a cycle time of 7 seconds, for example, using a solution with linolenic concentration of 0.1%. Using cystamine dihydrochloride as the derivitizing agent, the electrode derivitization can advantageously be conducted in a cycle time of 7 seconds, for example, using a solution of 0.2%. Optionally, assay buffer solution may then be passed through the cell, e.g., at the same flow rate and time period, before the sample solution is introduced, in order to remove residual derivitizing agent, e.g. derivitizing agent which does not bind to the electrode. Also, optionally, assay buffer solution may be passed through the cell after introduction of the sample solution but before release of the magnet and luminescence measurement, e.g., at a rate of 2.5 ml/min for 20 seconds. Other flow rates and time periods may be used and electrochemical parameters altered to obtain varied electrode surface derivitizations, for example.

The apparatus and method of the present invention are not limited to particular sample compositions. The samples may be solid, emulsions, suspensions, liquids or gases and may be derived from various sources such as cells, water, organic solvents, air and the like, such as those described in PCT 92/00982. The sample composition contains an analyte of interest which can vary widely from cells, subcellular particles, viruses, haptens, antigens, antibodies, nucleic acids, proteins, and the like, such as those described more particularly in PCT 92/00982. Typically, the analyte of interest is present at low concentrations of less than about $10^{-3}$ molar and can be as low as $10^{-12}$ molar or lower. In some embodiments, the analytes of interest are capable of entering into a binding reaction such as a DNA or RNA interaction, an antigen-antibody reaction, a ligand receptor reaction and the like. This binding reaction may allow for the incorporation of a label, such as an ECL-active label, thus providing an ECL-active species. The labels may be incorporated on the analyte directly, on a binding partner, or through another reacting component. An alternative to labeling the analyte of interest directly or indirectly is to label an analog thereof which competes with the analyte. The use of binding partners and analogs of the analyte of interest is described more particularly in WO92/14138 where they are referred to as "assay-performance-substances".

Advantageously, the ECL-active moieties used as labels are, metal chelates. Essentially any metal chelate which will luminesce under electrochemical conditions can be used as an ECL-active moiety. The metal can be, for example, a transition metal, such as a d-block transition metal, or a rare earth metal. Suitable transition metals include those selected from the group consisting of osmium, ruthenium, iridium, rhodium, platinum, indium, palladium, molybdenum, technetium, copper, chromium, or tungsten. Preferred transition metals are ruthenium and osmium. The ligands which are linked to the metal of such metal chelates are usually heterocyclic or organic in nature and play a role in determining solubility. Examples of suitable ligands are the polydentate ligands and monodentate ligands described in WO92/14138. Examples of suitable metal chelates are as follows: bis[(4,4'-carbomethoxy)-2,2'-bipyridine] 2-[3-(4-methyl-2,2'-bipyridine-4-yl)propyl]-1,3-dioxolane ruthenium (II); bis (2,2'-bipyridine) [4-(butan-1-al)-4'-methyl-2,2'-bipyridine] ruthenium (II); bis (2,2'-bipyridine) [4-(4'-methyl-2,2'-bipyridine-4'-yl)-butyric acid] ruthenium (II); tris (2,2'-bipyridine) ruthenium (II); (2,2'-bipyridine) [bis-bis(1,2-diphenylphosphino) ethylene]2-[3-(4-methyl-2,2'-bipyridine-4'-yl)propyl]-1,3-dioxolane osmium (II); bis(2,2'-bipyridine) [4-(4'-methyl-2,2'-bipyridine)-butylamine] ruthenium (II); bis(2,2'-bipyridine) [1-bromo-4(4'-methyl-2,2'-bipyridine-4-yl)butane] ruthenium (II); bis (2,2'-bipyridine)maleimidohexanoic acid, 4-methyl-2,2'-bipyridine-4'-butylamide ruthenium (II). Other suitable ECL active moieties are described in WO 92/14138, WO 88/0394 and WO 87/00987.

Preferred ECL-active moieties are those with tris(2,2'-bipyridine) ruthenium (II) which can undergo an electrochemiluminescent reaction with tripropylamine (TPA). The salts of ruthenium (II) tris(bipyridyl) are very stable, water soluble compounds which be chemically modified with reactive groups to form active moieties such as ,the $Ru(bpy)_3^{2+}$ NHS ester of formula I below.

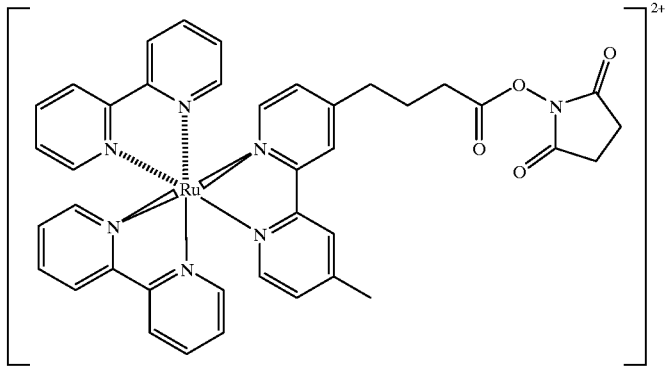

Figure 4:
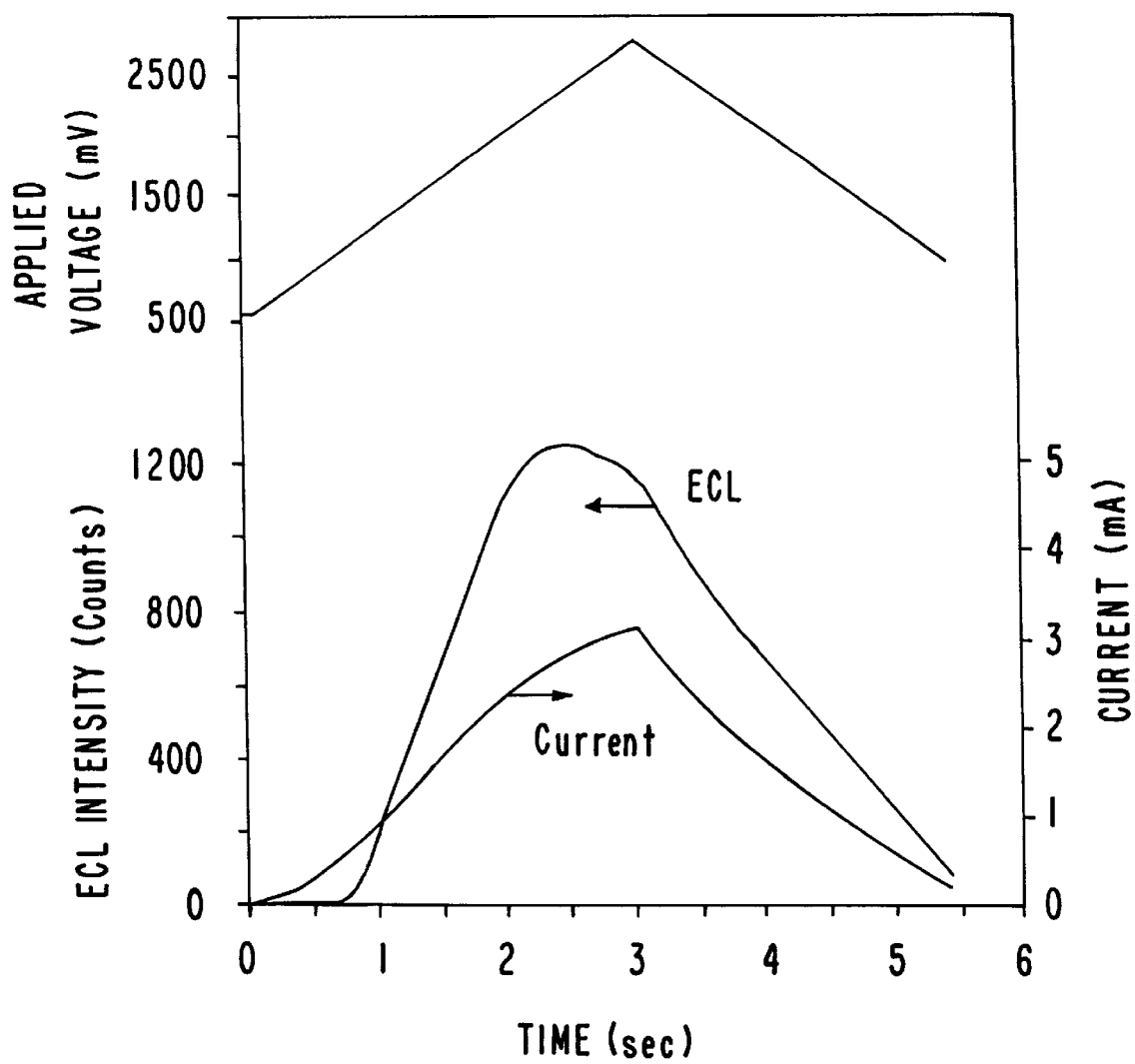
FIG. 4 is a graph of working electrode current and ECL intensity induced by the application of a triangle wave to the electrodes of an Origen® 1.5 analyzer with a Ru(bpy)$_3^{2+}$ NHS ester with TPA.

These moieties can be bound to proteins, haptens, nucleic acids, etc. The ECL reaction of the ECL-active species within the sample composition is initiated by an applied voltage. Many different voltage wave forms can be applied to initiate the ECL reaction. FIG. 4 illustrates measurements of the working electrode current and ECL intensity induced by the application of a triangle wave to the electrodes of an Origen® 1.5 analyzer with $Ru(bpy)_3^{+2}$ NHS ester of formula I above with TPA. The applied voltage as shown is actually the voltage measured at the reference electrode and includes the effects of a significantly uncompensated resistance; consequently, the actual voltage applied at the working electrode is substantially less than that depicted. The current that flows in the cell prior to applying a voltage to the electrodes is primarily the result of the oxidation of the TPA and of the hydrolysis of water. The electrochemiluminescent reaction becomes evident when the applied voltage reaches approximately 1100 mAs. The intensity of the luminescence is shown to increase with the applied voltage until the TPA at the surface of the electrode is depleted and/or oxygen-quenching begins. The observed luminescence illustrated in FIG. 4 can be easily measured with conventional photomultiplier tubes.

As can be appreciated by one of ordinary skill in the art, the amount of metal chelate or other metal containing ECL moiety incorporated in the sample composition can vary widely from system to system. Generally, the amount of moiety utilized is that which is effective to result in the emission of a detectable and, if desired, quantifiable emission of electromagnetic energy from the sample composition. The detection and/or quantitation of an analyte of interest is typically made and compared to luminescence from the sample containing a known amount of analyte of interest as a calibration standard.

When magnetic particles are used bound to the ECL moiety, they advantageously comprise microparticulate matter having a diameter of 0.0001 to 200 µm. These microparticles must be magnetically responsive to and typically comprise iron dioxide, or other oxides of iron. The surface of the microparticles must contain a component capable of binding to the analyte of interest, an analog thereof or a binding partner. Suitable examples are described in WO92/14138. These include cross-linked starch, dextrans, proteins, and the like. The density of the particles can vary widely and may typically have a density of from 1.0 to 5.0 g/ml and preferably have a density of from 1.1 to 2 g/ml. The concentration of the particles used in preparing the sample composition also vary widely such as, for example, 1–10, 000 mg/ml, preferably 5–1000 mg/ml. Suitable magnetic particles are described in U.S. Pat. Nos. 4,628,037; 4,695, 392; 4,695,393; 4,698,302; 4,554,088; and EP 0 180 384. The particles may be paramagnetic or ferromagnetic. It is desirable that the magnetic particles have a low magnetic resonance so that when the magnetic field is removed from the electrode surface, the particles demagnetize and are swept from the cell. Examples of preferred particles are Dynal particles, particularly coated with a protein, obtained from Dynal A/S, Oslo, Norway. Specifically, they include Dynal 450-Tag-IgG particles, Dynal 280 particles, particularly coated with tag-oligo, and streptavidin-coated Dynal 280 particles, for example, biotinylated TAG-antibody bound to streptavidin-coated 280 particles.

In order to introduce electrochemical energy to the ECL-active species in the sample composition, the electrode may be immersed in an electrolyte, i.e., assay buffer solution, which typically is a solution of one or more salts or other species in water, an organic liquid or mixture thereof. Suitable examples are given in WO92/14138.

A variety of assays can be performed using the methods of this invention. The methods of this invention are capable of measuring trace amounts of microorganisms, pharmaceuticals, hormones, viruses, antibodies, nucleic acids and other proteins, for example.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

The entire disclosures of all applications, patents and publications, cited above and below, are hereby incorporated by reference.

EXAMPLES

Instrumentation

An ECL-detection apparatus as shown in FIGS. 1–3 is employed in the examples illustrating the invention. The fluid handling components, luminometer, potentiostat and electrochemical flow cell of each apparatus are those of an Origen 1.5 analyzer with the following features, unless indicated otherwise:

Working electrode—Au rectangle, 6 mm width

Counter electrode—Au rectangle, 6 mm width

Reference electrode—Ag/AgCl cell gap—12 mils.

Components of Sample Composition

ECL moiety—Ru(bpy)$_3^{2+}$-NHS ester=Ru(2,2'-bipyridyl)$_2$(4-[3-(1,3-dioxolan-2-yl)propyl]-4'-methyl-2,2'-bipyridine)$^{2+}$ obtained from Igen, Inc.

ECL buffer—112 mM KH$_2$PO$_4$, 88 mM K$_2$HPO$_4$·3H$_2$O, 50 μm NaCl, 6.5 mM NaN$_3$, 0.8 μm Triton X-100, 0.4 mM Tween 20, 100 mM tripropylamine H$_2$O.

ECL diluent—37.5 mml KH$_2$PO$_4$, 109.2 mM K$_2$HPO$_4$·3H$_2$O, 151.7 mM NaCl, 0.65 mM NaN$_3$, 0.43 mM bovine serum albumin in H$_2$O.

Microparticles a) Dynal M-450 Dynabead, 4.5 μM diameter superparamagnetic particles, 30 mg/mL obtained from Dynal, 45 North Station Plaza, Great Neck, N.Y. 11021.

b) Dynal M-280 Dynabeads, 2.8 μM diameter superparamagnetic particles, 10 mg/mL, obtained from Dynal, 45 North Station Plaza, Great Neck, N.Y. 11021.

Coated Microparticles

The microparticles (Dynal beads M-280) are coated with protein by mixing 1 mL (30 mg) of particles in 150 micro moles/liter sodium carbonate bicarbonate buffer (pH 9.6) with an equal volume of 0.5 to 1.0 g/L of protein solution. This protein solution is incubated for 15 minutes at 37° C. The particles are then separated and incubated for 15 minutes in the ECL diluent described above.

Labeled Antibodies

To label antibodies with Ru(bpy)$_3^{2+}$ 1 mg of antibody and 0.5 mL of the phosphate-buffered saline (pH 7.8) with 3 mL of 5.0 g/L Ru(bpy)$_3^{2+}$-NHS ester anhydrous dimethyl sulfoxide are mixed. Labeling is allowed to proceed for 30 minutes and then terminated by the addition of 25 μl of 1.0 m/l glycine reagent and further incubated for 10 minutes. The labeled protein is then purified by passage through a Sephadex G25 column, eluted with phosphate buffered saline (pH 7.2) containing a sodium azide, 0.5 g/L. The Ru(bpy)$_3^{2+}$ labeled protein fractions are collected and pooled. The immunoassays can be performed by mixing 100 mL of sample, 75 mL of coated microparticles and 75 mL of labeled antibody and incubating the mixture with agitation for 15 minutes.

ECL Measurement Cycle

The ECL measurement cycle comprises at least four steps: 1) pre-conditioning; 2) derivitizing the electrode, 3) measuring; and 4) cleaning. The preconditioning step involves the application of a voltage triangle wave form of 0.0–2.2 volts to −1.0 to +0.6 volts at 2.0 v/sec. The derivitizing step involves the application of a constant voltage of from 0 to 565 mV. The measurement step involves the application of a triangle wave form of +0.6 volts to +2.8 volts at +2.0 volts to 1.0 volts per second. The cleaning step involves the application of a voltage square wave from 0.0 to 3.0 volts to −0.5 to 0.0 volts. All voltages are relative to the Ag/AgCl reference electrode.

Example 1

An Origen 1.5 analyzer, as described above, is preconditioned by flowing an assay buffer solution through the sample cell. A derivitizing solution containing 0.03% sodium oleate as the derivitizing agent in assay buffer solution is flowed through the sample cell and contacted with the electrodes at a flow rate of 2.5 ml/min for 10 seconds while maintaining a voltage of 565 mV, the pre-operative potential or POP, across the working electrode surface. While maintaining the 565 mV voltage, assay buffer solution is then flowed through the sample cell also at a flow rate of 2.5 ml/min for 10 seconds. A magnetic field is applied to the sample cell by the magnets and the sample solution is flowed through the sample cell at a flow rate of 2.5 ml/min for 25 seconds. While the sample is still being magnetically held additional assay buffer is flowed through at 2.5 ml/min for 20 seconds. The magnetic field is then removed and a measuring ramp voltage of about 2800 mV applied at 2000 mV/sec across the working electrode surface and the luminescence generated from ECL-active species is measured.

Figure 5:
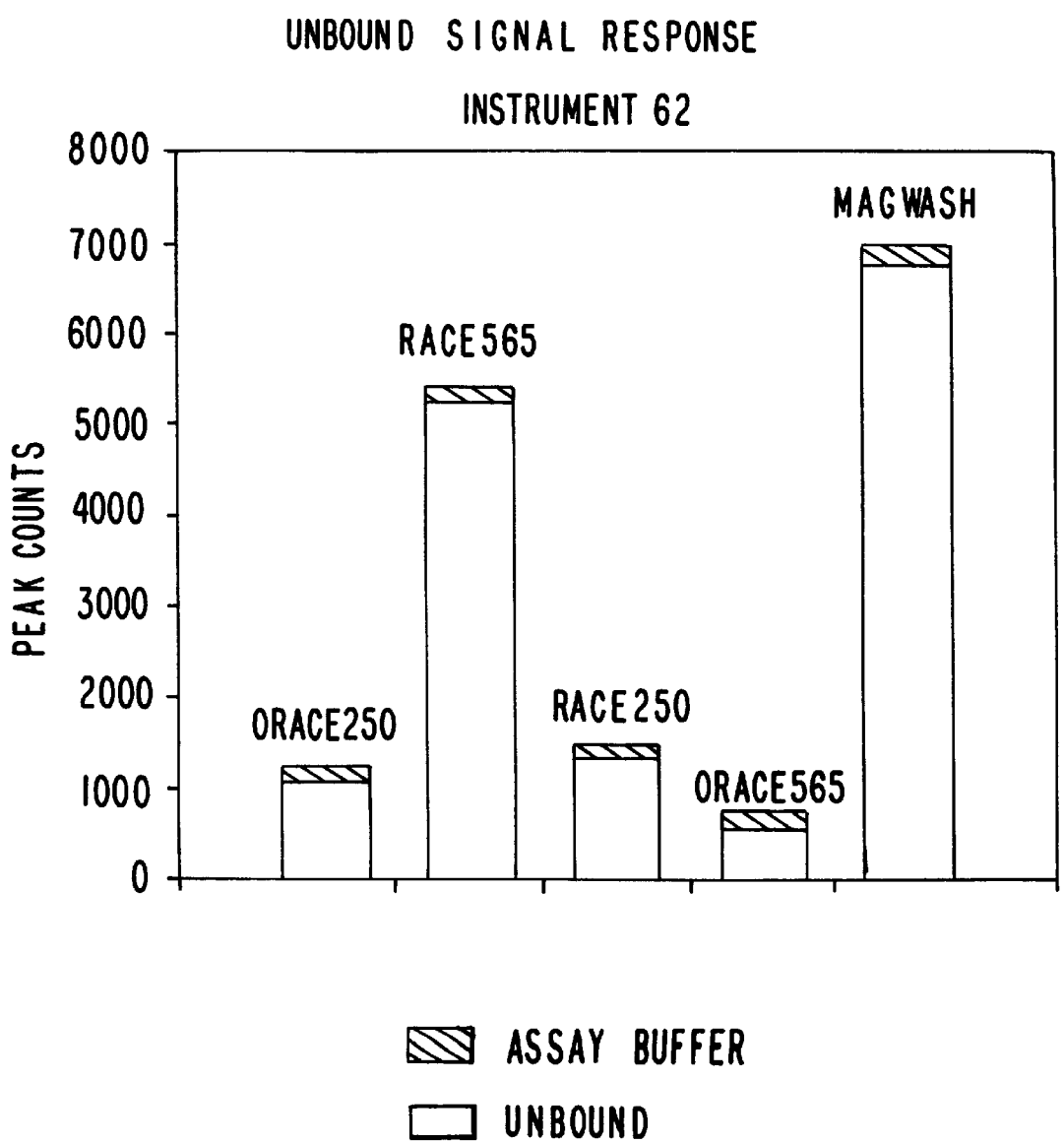
FIG. 5 is a bar graph of the unbound signal response results of Example 1 below.
Figure 6:
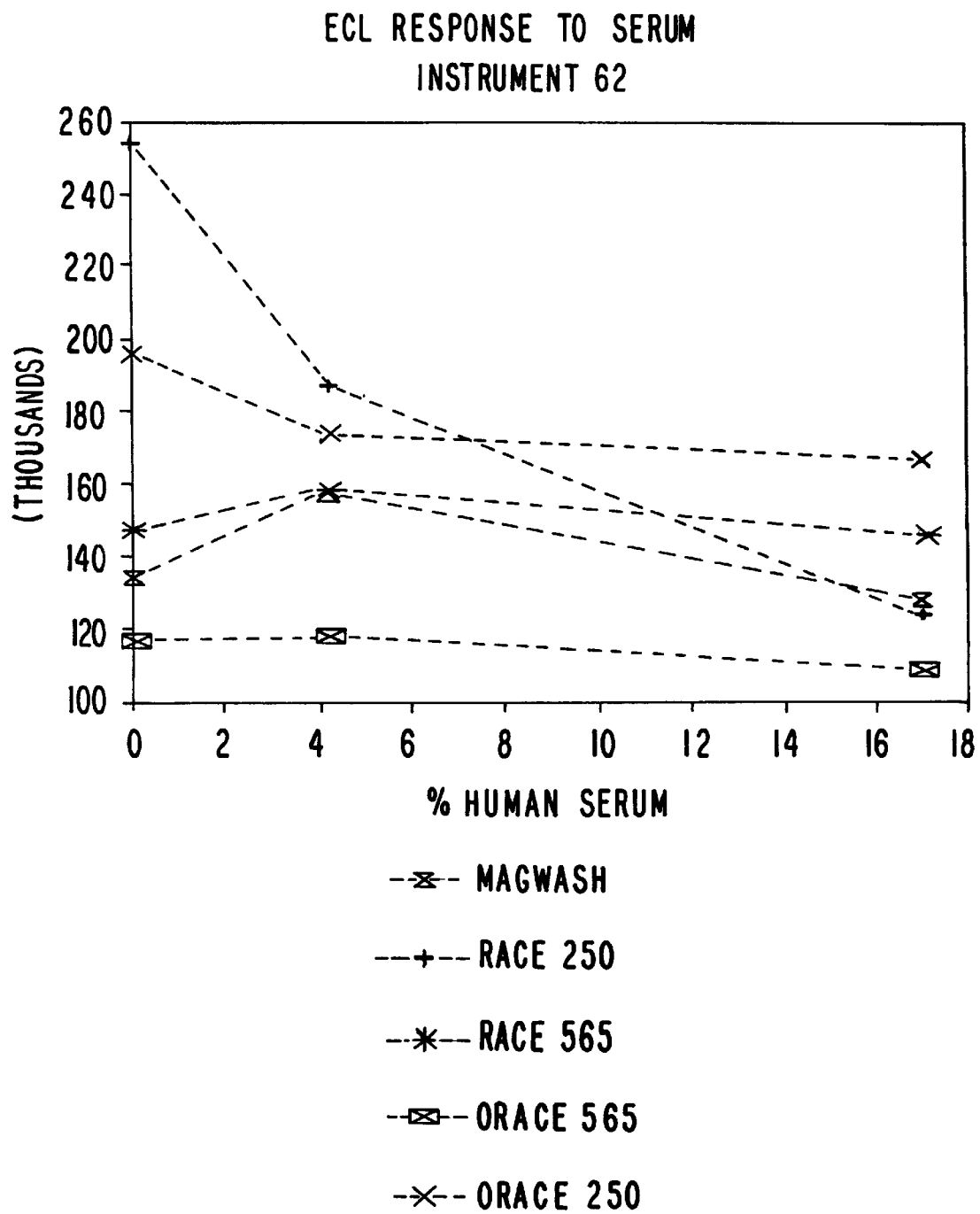
FIG. 6 is a graph of ECL Response to human serum according to Example 1 below.
Figure 7:
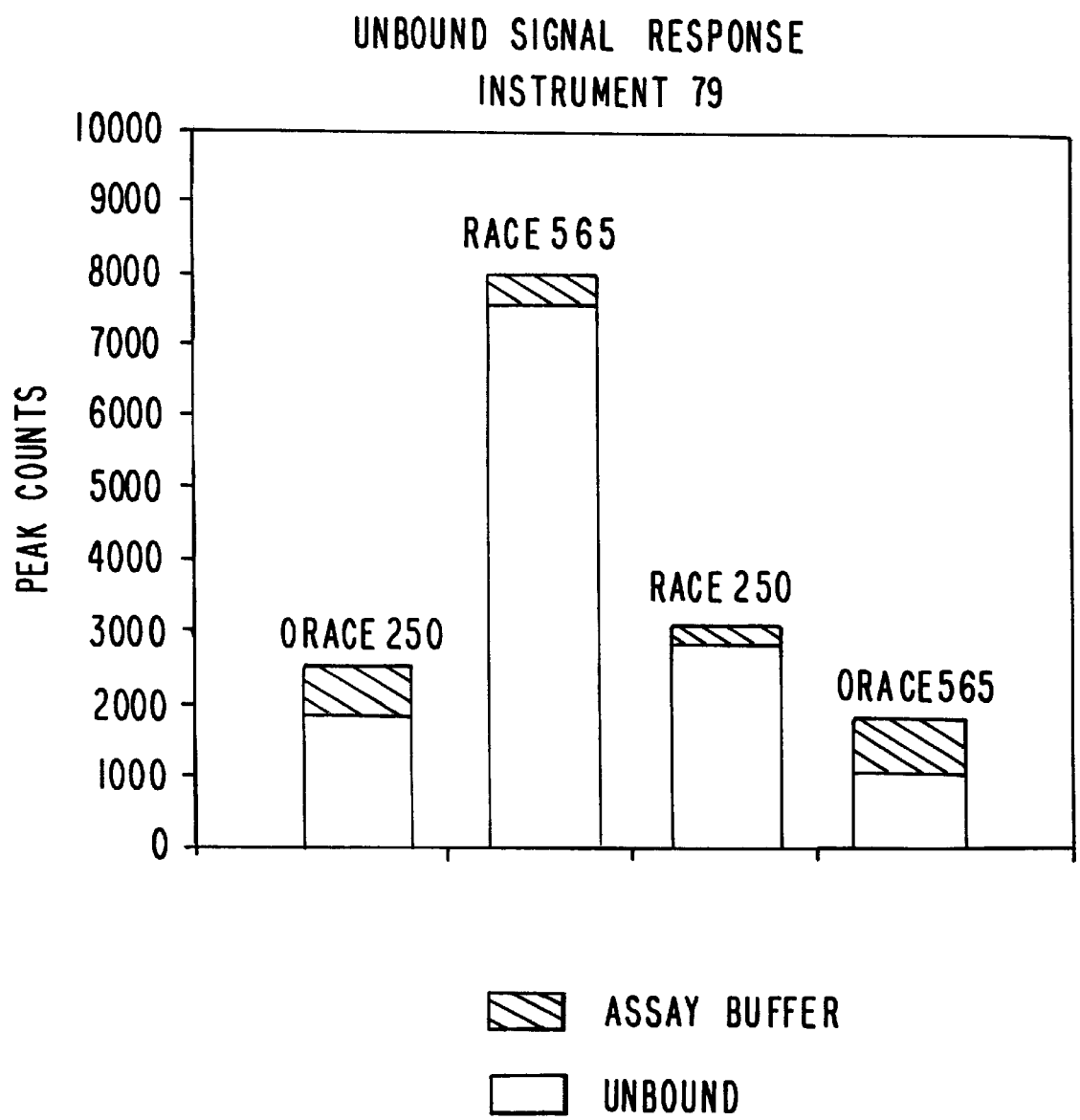
FIG. 7 is a bar graph of the unbound signal response results of Example 1 below.
Figure 8:
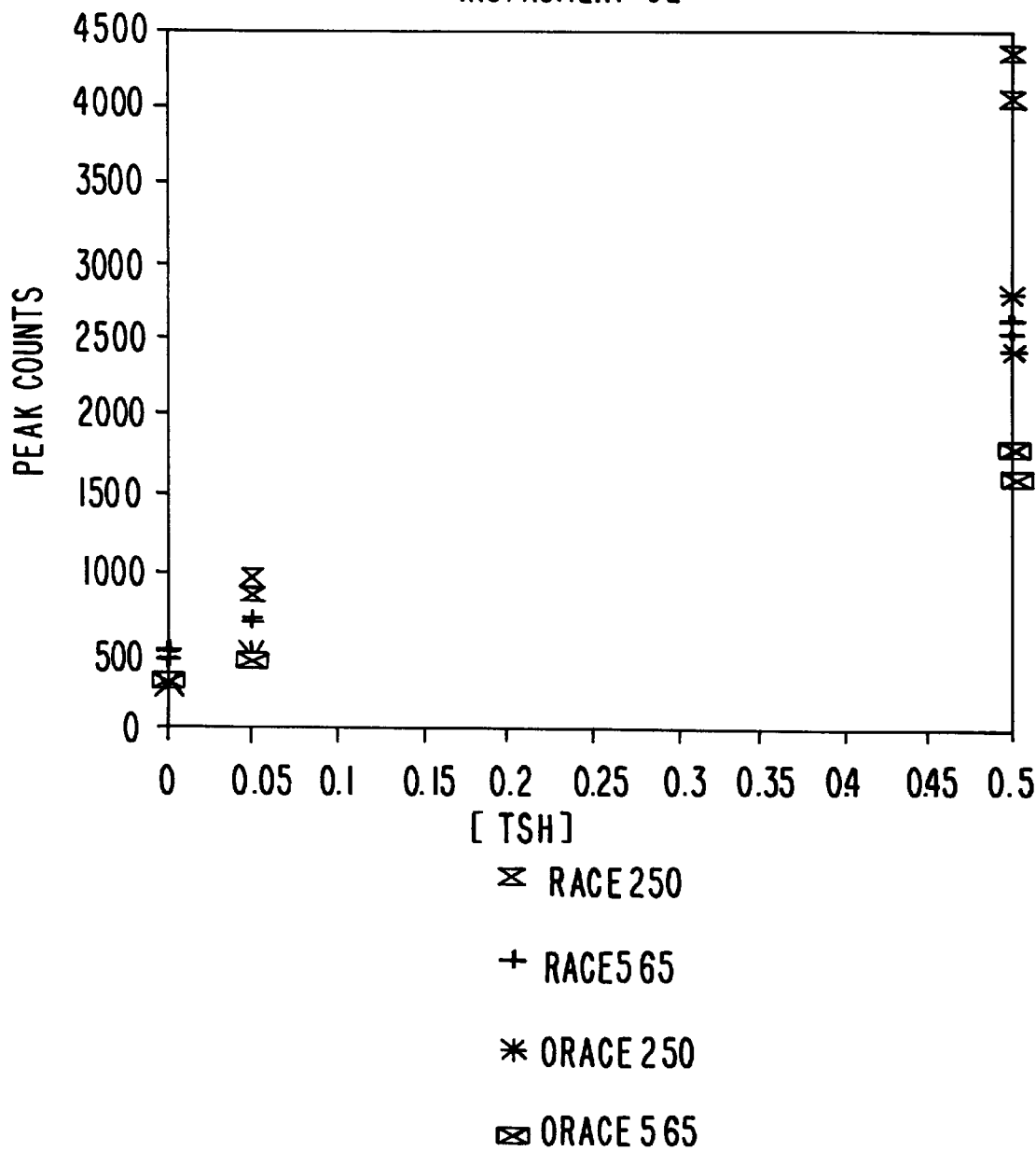
FIG. 8 shows the TSH response to derivitization according to Example 1 below.
Figure 9:
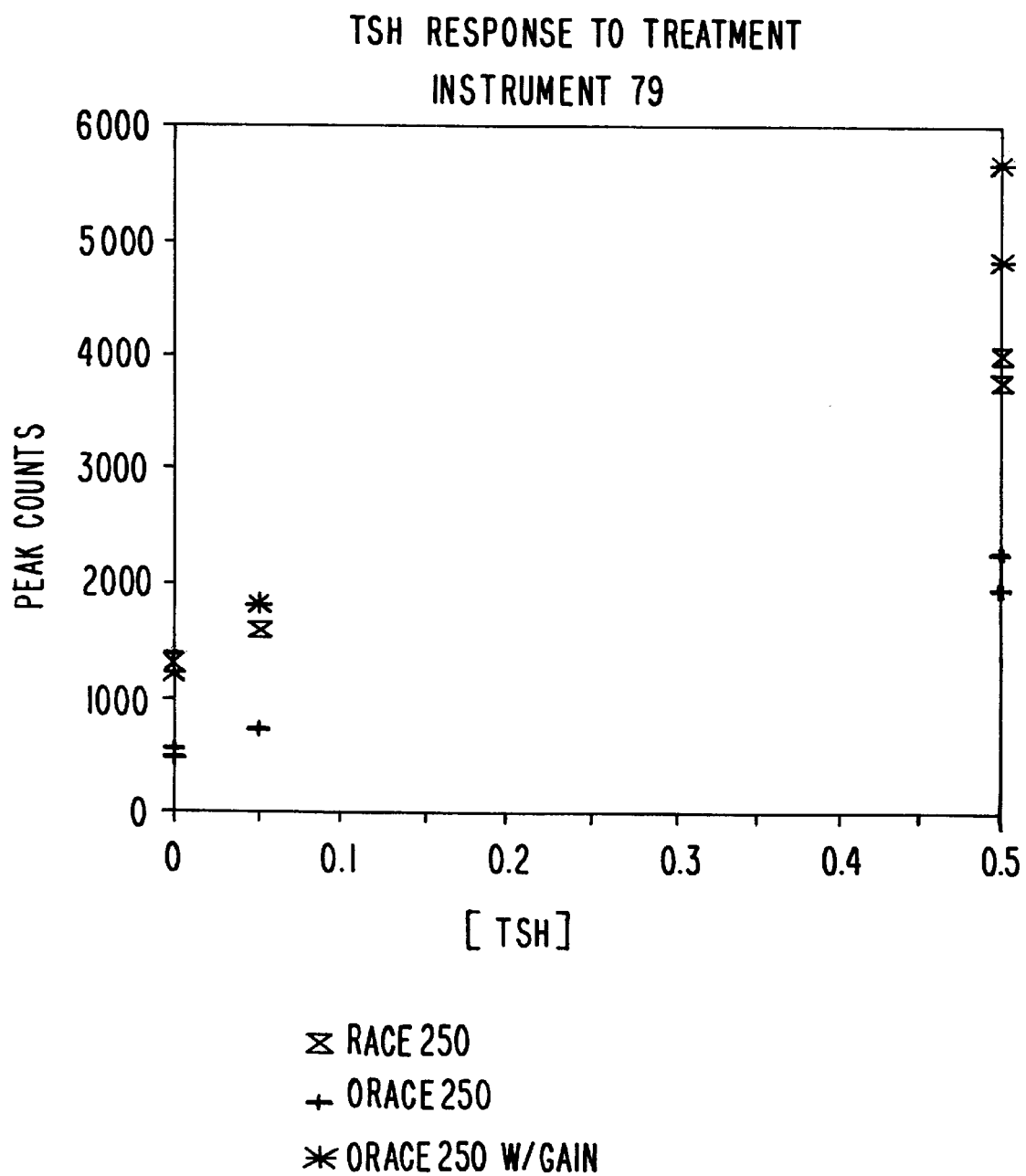
FIG. 9 shows the TSH response to derivitization according to Example 1 below.

Using this procedure, a first set of experiments was conducted to measure by ECL the derivitizing effect of different oleate concentrations on samples of buffer blank, ruthenium-labeled mouse IgG and ruthenium-labeled IgG coated (Dynal 4.5 μm) magnetic particles. These results were positive in that the magnetic particle signal is not effected significantly, but the background signal is significantly reduced, as is shown in the attached FIGS. 5, 6 and 7. Therein, orace250 indicates a test with an electrode derivitized with oleate at a POP of 250 mV and race250 indicates a parallel test with an underivitized electrode at a POP of 250 mV. The orace565 indicates a test with an oleate derivitized electrode at 565 mV POP-and race565 is a parallel test with underivitized electrode at 565, mV POP. The magwash results indicate a test similar to race565, i.e., with an underivitized electrode, but with a higher sample volume and a slower scan rate, which accounts for the somewhat higher signal response, but otherwise comparable results to race565. The results were verified in two separate tests on separate instruments. Also, human TSH, i.e., thyroid stimulating hormone (an analyte), serum samples were measured and the results shown in attached FIGS. 8 and 9.

Example 2

Figure 10:
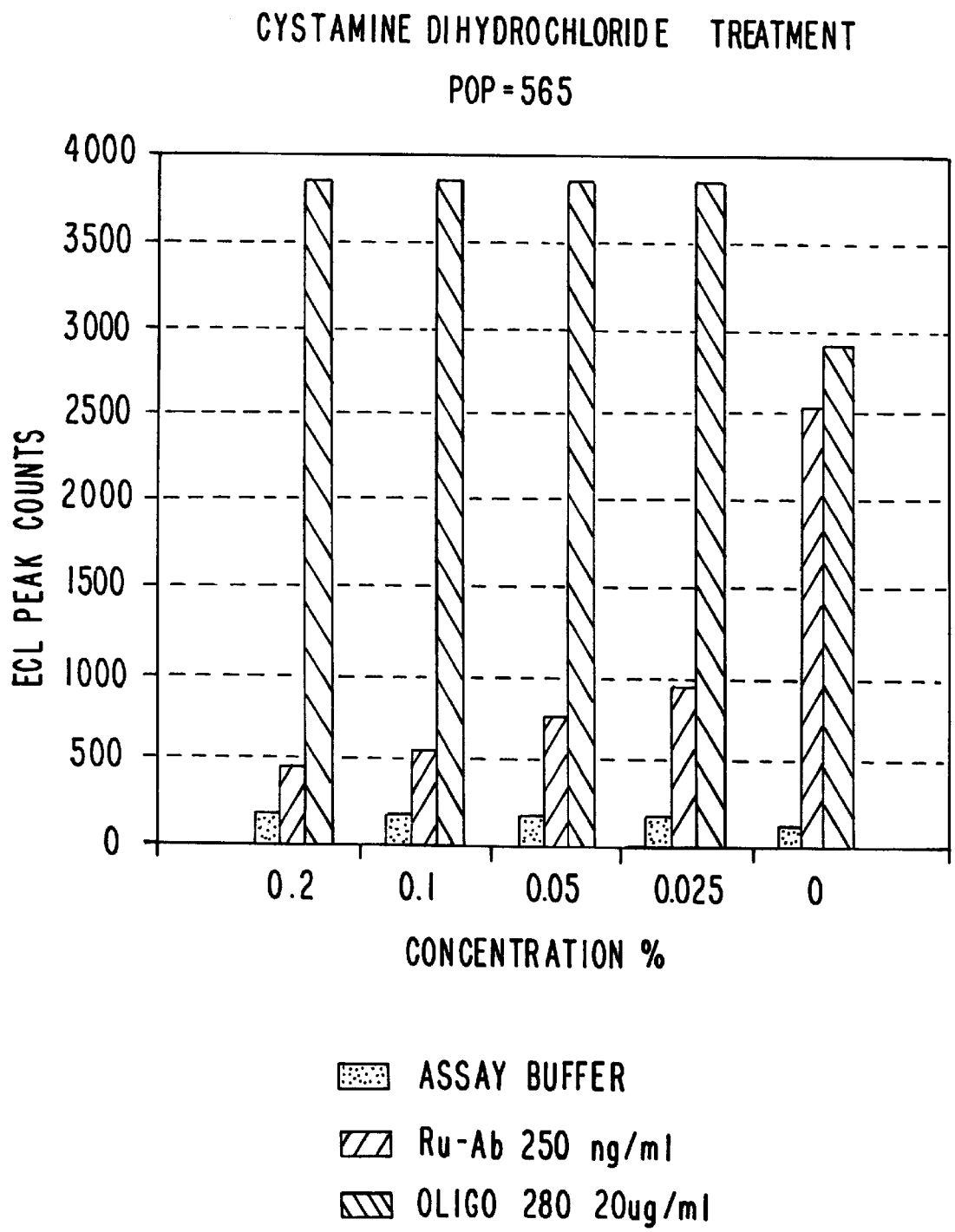
FIG. 10 is a bar graph of the results with cystamine dihydrochloride derivitization according to Example 2 below.

With clean, conditioned electrodes, and prior to aspirating the sample, on-line chemical derivitization of gold electrodes is achieved by flowing 100 μl of cystamine dihydrochlodide/assay buffer solution (0.01%–0.2%), at 2.5 ml.min, through the detection cell while maintaining 565 mV across the working electrode surface. Continuing to apply 565 mV, 500 μl of assay buffer is then pumped through at a flow rate of 2.5 ml/min to remove any "free" residual cystamine. The sample is then pumped to the electrodes for ECL measurement, as described herein. FIG. 10 shows various amounts of cystamine used to treat electrodes with each amount giving corresponding 250 ng/ml ruthenium-labeled IgG signal response without adversely affecting the assay buffer and ruthenium-labeled particle signals.

Example 3

Figure 11:
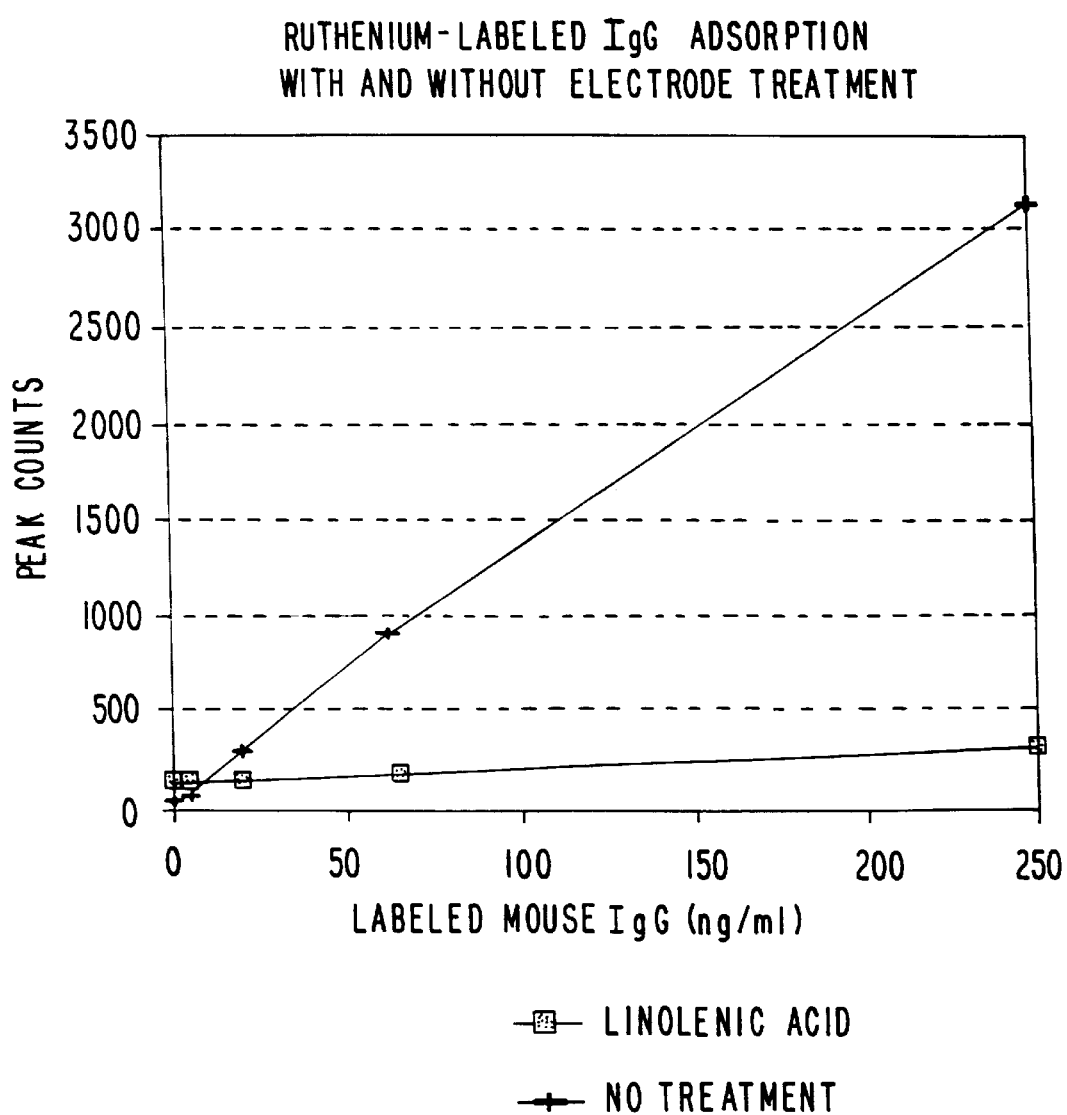
FIG. 11 is a graph of the results with linolenic acid derivitization according to Example 3 below.

With clean, conditioned electrodes, and prior to aspirating the sample, on-line chemical derivitization of gold electrodes is achieved by flowing 100 μl of 0.1% linolenic acid/assay buffer solution, at 2.5 ml/min, through the detection cell while maintaining 565 mV across the working electrode surface. Continuing to apply 565 mV, 500 μl of assay buffer is then pumped through at a flow rate of 2.5 ml/min for 25 seconds to remove any "free" residual linoleneate, and then assay buffer is pumped at 4.5 ml/min for 6 seconds. The sample is then pumped to the electrodes for ECL measurement. FIG. 11 shows that when electrodes are treated with linoleneate, there is a negligible increase over blank shown by the ruthenium-labeled IgG concentration response signal.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

What is claimed is:

1. A method for determining the presence or absence of an analyte, said method comprising:
   a) contacting a working electrode with a derivitizing solution consisting essentially of a derivitizing agent, said derivitizing agent being a fatty acid or a salt thereof, a short-chain aminated thiol, or a surfactant, a derivitizing-effective voltage being imposed across the electrode so that the derivitizing agent binds to the electrode;
   b) contacting with said derivatized electrode an assay solution comprising the sample, an electrochemiluminescent label capable of binding with said analyte of interest, and non-analyte interfering compounds, wherein the electrochemiluminescent label is a metal chelate;
   c) imposing an electrochemical voltage upon the derivatized working electrode causing the electrochemiluminescent label to emit electrochemiluminescence; and
   d) detecting or measuring emitted luminescence as an indication of whether or in what amount said analyte is present in the sample.

2. The method according to claims 1, wherein the working electrode is caused to be in contact with said derivitizing solution prior to imposition of said derivitizing-effective voltage.

3. The method according to claim 1, wherein said derivitizing-effective voltage is imposed prior to contacting said electrode with said derivitizing solution.

4. The method according to claim 1, wherein the derivitizing solution consists essentially of linolenic acid, linoleic acid, oleic acid, eicosatrienoic acid, undecylenic acid, stearic acid, or capric acid or salts thereof or cystamine hydrochloride.

5. The method according to claim 1, wherein the derivitizing agent is contained in a derivitizing solution in an amount of 0.01 to 0.2 percent.

6. The method according to claim 1, wherein a voltage of 0 to 565 mV is applied to the electrode while it is in contact with the derivitizing solution.

7. The method according to claim 1, wherein the derivitizing solution consists essentially of an amine-terminated thiol containing 1 to 6 carbon atoms.

8. The method according to claim 1, wherein the derivitizing solution consists essentially of 4-lauryl ether, dodecyl maltoside or tetramethyl-5-decyn-4,7-diol.

9. The method according to claim 1, wherein the derivitizing solution consists essentially of cystamine dihydrochloride.

10. The method according to claim 1, wherein the metal in the metal chelate is osmium or ruthenium.

11. The method according to claim 1, wherein the metal chelate is bis[4,4'-carbomethoxy)-2,2'-bipyridine] 2-[3-(4-methyl-2,2'-bipyridine-4-yl)propyl]-1,3-dioxolane ruthenium (II); bis (2,2'-bypyridine) [4-(butan-1-al)-4'-methyl-2,2'-bipyridine] ruthenium (II); bis(2,2'-bipyridine) [4-(4'-methyl-2,2'-bipyridine-4'-yl)-butyric acid] ruthenium(II)i tris (2,2'-bipyridine) ruthenium (II); (2,2'-bipyridine)[bis-bis (1,2-diphenylphosphino)ethylene] 2-[3-(4-methyl-2,2'-bipyridine-4'-yl)propyl]-1,3-dioxolane osmium (II); bis(2,2'-bipyridine) [4-(4'-methyl-2,2'-bipyridine)-butylamine] ruthenium (II); bis(2,2'-bipyridine) [1-bromo-4(4'-methyl-2,2'-bipyridine-4-yl)butane] ruthenium II; or bis (2,2'-bipyridine)maleimidohexanoic acid, 4-methyl-2,2'-bipyridine-4'-butylamide ruthenium (II).

12. The method according to claim 1 wherein the non-analyte interfering compounds are serum matrix components, unbound electrochemiluminescent labels not connected to analyte, or mixtures thereof.

13. The method according to claim 12, wherein the non-analyte interfering compounds are unbound electrochemiluminescent labels.

14. The method according to claim 12, wherein the non-analyte interfering compounds are serum matrix components.

15. The method according to claim 1, wherein magnetic microparticles are bound to the electrochemiluminescent label and the analyte is magnetically localized at the derivatized working electrode prior to imposing electrochemical voltage on the working electrode to cause the electrochemiluminescent label to emit electrochemiluminescence.

16. The method according to claim 15, wherein the derivitizing solution flows across the working electrode while constant voltage is applied to the working electrode.

17. The method according to claim 15, wherein the derivitizing agent is sodium oleate; the flow rate of the derivitizing solution is 2½ milliliters per minute, and a constant voltage of 565 millivolts is applied to the working electrode for 10 seconds.

18. The method according to claim 15, wherein the derivitizing agent is cystamine dihydrochloride; the flow rate of the derivitizing solution is 2 ½ milliliters per minute; and a constant voltage of 565 millivolts is applied to the working electrode for 10 seconds.

19. The method according to claim 15, wherein the derivitizing agent is linolenic acid; the flow rate of the derivitizing solution is 2½ milliliters per minute; and a constant voltage of 565 millivolts is applied to the working electrode for 10 seconds.

20. The method according to claim 1 wherein the electrode is Pt or Ag.

21. The method according to claim 1, wherein said electrochemiluminescent label is capable of directly binding with said analyte of interest.

22. The method according to claim 1, wherein said electrochemiluminescent label is capable of indirectly binding with said analyte of interest.

* * * * *

UNITED STATES PATENT AND TRADEMARK OFFICE
CERTIFICATE OF CORRECTION

PATENT NO. : 6,132,955
DATED : October 17, 2000
INVENTOR(S) : Talley et al.

It is certified that error appears in the above-identified patent and that said Letters Patent is hereby corrected as shown below:

Column 16,
Line 8, change "ruthenium (II)i" to -- ruthenium (II); --.

Signed and Sealed this

Second Day of April, 2002

Attest:

JAMES E. ROGAN
*Attesting Officer*         *Director of the United States Patent and Trademark Office*